US010288188B2

(12) United States Patent
Schieweck et al.

(10) Patent No.: US 10,288,188 B2
(45) Date of Patent: May 14, 2019

(54) ELECTROMAGNETICALLY OPERATED VALVE

(71) Applicants: FRESENIUS MEDICAL CARE DEUTSCHLAND GMBH, Bad Homburg (DE); RAUSCH & PAUSCH GMBH, Seib (DE)

(72) Inventors: Werner Schieweck, Thierstein (DE); Werner Doehla, Gefrees (DE); Olaf Seewald, Bayreuth (DE); Michael Teichmann, Bayreuth (DE)

(73) Assignees: FRESENIUS MEDICAL CARE DEUTSCHLAND GMBH, Bad Homburg (DE); RAUSCH & PAUSCH GMBH, Selb (DE)

( * ) Notice: Subject to any disclaimer, the term of this patent is extended or adjusted under 35 U.S.C. 154(b) by 0 days.

(21) Appl. No.: 15/302,631

(22) PCT Filed: Mar. 23, 2015

(86) PCT No.: PCT/EP2015/056082
§ 371 (c)(1),
(2) Date: Oct. 7, 2016

(87) PCT Pub. No.: WO2015/154974
PCT Pub. Date: Oct. 15, 2015

(65) Prior Publication Data
US 2017/0211718 A1    Jul. 27, 2017

(30) Foreign Application Priority Data
Apr. 8, 2014    (DE) .................. 10 2014 005 137

(51) Int. Cl.
*F16K 31/06*    (2006.01)
*A61M 39/22*    (2006.01)
(Continued)

(52) U.S. Cl.
CPC ....... *F16K 31/0675* (2013.01); *A61M 1/1621* (2014.02); *A61M 39/22* (2013.01);
(Continued)

(58) Field of Classification Search
CPC ............ F16K 31/0648; F16K 31/0655; F16K 31/0668; F16K 31/0672; F16K 31/0675;
(Continued)

(56) References Cited

U.S. PATENT DOCUMENTS 5,127,625 A * 7/1992 Kleinhappl ............. F16K 31/06
251/129.17
5,165,652 A * 11/1992 Nicolaisen .......... F16K 31/0689
251/129.17
(Continued)

FOREIGN PATENT DOCUMENTS

CN        2797789     7/2006
CN      102338242     2/2012
(Continued)

OTHER PUBLICATIONS

Machine Translation of WO 9715771.*
PCT/EP2015/056082 International Search Report.

*Primary Examiner* — Ian G Paquette
(74) *Attorney, Agent, or Firm* — Jacobson Holman, PLLC.

(57) ABSTRACT

An electromagnetically operated valve, comprises a valve slide with a magnet armature, which is equipped to close a sealing seat in a fluid channel of the valve with a first axial end in a closed position, as well as a sealing element with folded bellows situated between the sealing seat and the first axial end of the valve slide and separates the valve slide from the fluid channel with a fluid-tight seal. The magnet armature is supported in the valve in an essentially non-contact manner due to the fact that the valve slide has a guide pin protruding in the axial direction from the magnetic
(Continued)

armature on a second axial end opposite the first axial end, the guide pin being supported to slide in the axial direction; and the valve slide is aligned in the radial direction on a side of the magnet armature facing the first axial end of the valve slide and is supported so it is movable in the axial direction by means of at least one spring element.

17 Claims, 2 Drawing Sheets

(51) Int. Cl.
  *F16K 41/10* (2006.01)
  *A61M 1/16* (2006.01)
  *F16K 1/46* (2006.01)
  *F16K 15/02* (2006.01)
(52) U.S. Cl.
  CPC .............. *F16K 1/46* (2013.01); *F16K 15/026* (2013.01); *F16K 31/0655* (2013.01); *F16K 41/103* (2013.01)
(58) Field of Classification Search
  CPC .............. F16K 31/0686; F16K 31/0689; F16K 31/0696; F16K 1/46; F16K 15/026; F16K 41/103; A61M 39/22; A61M 1/1621
  USPC ........................................ 251/129.15, 129.17
  See application file for complete search history.

(56) References Cited

U.S. PATENT DOCUMENTS

| | | | | |
|---|---|---|---|---|
| 5,651,528 A | * | 7/1997 | Frei | F16K 31/0689 251/335.3 |
| 5,707,039 A | * | 1/1998 | Hamilton | F16K 31/0655 251/129.15 |
| 8,672,292 B2 | * | 3/2014 | Leiser | F16K 31/0689 251/129.15 |
| 2005/0173664 A1 | | 8/2005 | Ogawa | |
| 2014/0166916 A1 | * | 6/2014 | Buse | F02B 37/186 251/186 |
| 2014/0367595 A1 | * | 12/2014 | Miura | F16K 31/0696 251/64 |
| 2015/0233487 A1 | * | 8/2015 | Matsumoto | F16K 31/0675 251/129.15 |

FOREIGN PATENT DOCUMENTS

| | | |
|---|---|---|
| CN | 203395336 | 1/2014 |
| DE | 23 03 450 A1 | 8/1974 |
| DE | 19953936 | 12/2000 |
| DE | 102007016736 | 11/2007 |
| DE | 102007005916 | 8/2008 |
| DE | 10 2011 077069 A1 | 12/2012 |
| DE | 202013104062 | 11/2013 |
| EP | 0801256 | 10/1997 |
| WO | WO 97/15771 A1 | 5/1997 |

\* cited by examiner

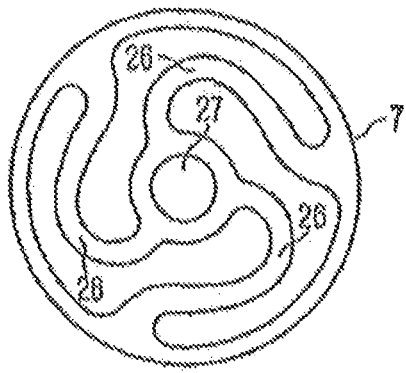
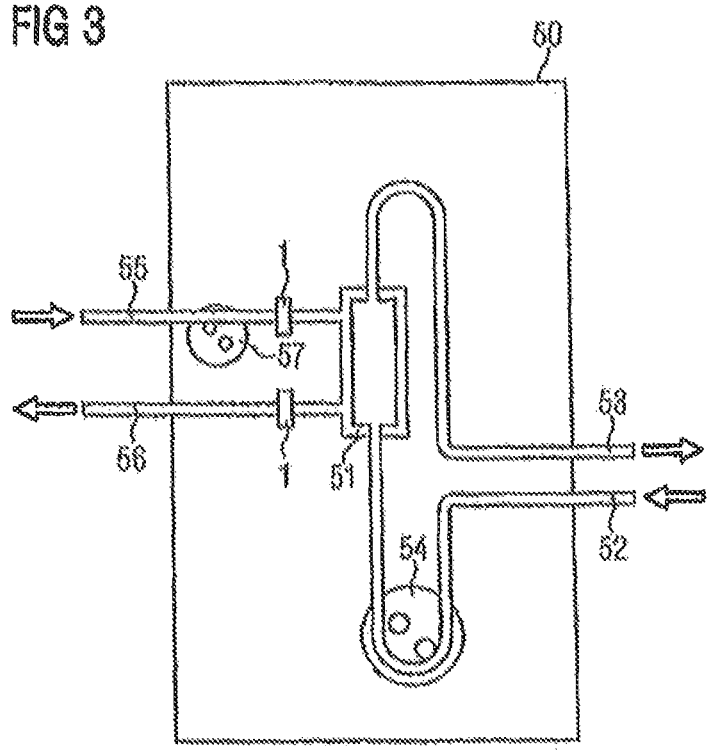

ELECTROMAGNETICALLY OPERATED VALVE

CROSS REFERENCE TO RELATED APPLICATIONS

This application is a National Stage of PCT application PCT/EP2015/056082, filed on Mar. 23, 2015, which claims priority to German application 10 2014 005 137, filed Apr. 8, 2014, the entirety of which is hereby incorporated by reference.

FIELD OF THE INVENTION

The invention relates to an electromagnetically operated valve, in particular for use in a device for providing an extracorporeal circulation for treating a patient, in particular for dialysis.

Electromagnetically operated valves are used to control the fluid flow in a fluid channel of devices for providing an extracorporeal circulation for treating a patient by dialysis in particular. For valves used in medical applications, it is important that the movable parts of the valve do not come in contact with the fluid. The fluid may be dialysis fluid (dialysate), for example. To this end, such valves usually have a sealing element, which serves to separate the drive of the valve from the fluid channel of the valve in a fluid-tight manner. The sealing element therefore has folded bellows, for example, to permit an axial mobility of the sealing element.

The valve additionally has a valve slide with a magnet armature, which can be displaced in the axial direction against a spring force by energization of a coil of the valve to move the valve slide into a closed position or out of the closed position, in which a sealing seat of the valve is sealed by means of the sealing element. The magnet armature is usually supported in a nonmagnetizable guide tube in the interior of the coil. This support causes frictional forces, which cause greater wear and must be overcome by the magnetic force. In addition, magnetic losses occur in the magnetic circuit of the magnetic drive of the valve due to the nonmagnetic guide tube.

SUMMARY OF THE INVENTION

It is therefore the object of the present invention to propose an electromagnetically operated valve in particular for use in a device for providing an extracorporeal circulation for treating a patient for dialysis in particular, such that it will overcome the disadvantages mentioned above, in particular losses and wear due to friction, as well as reducing magnetic losses.

This object is achieved by an electromagnetically operated valve according to the features of the independent claim 1. Refinements and advantageous embodiments are defined in the dependent claims.

According to the invention, the valve slide is preferably aligned by means of a spring element in the radial direction on a side of the magnet armature facing the sealing seat and is movably supported in the axial direction. In addition, the valve slide may have a guide pin protruding in the axial direction away from the magnet armature. The guide pin is preferably situated on an axial end of the valve slide opposite the sealing seat of the valve and has a surface with a reduced diameter in comparison with the outside diameter of the magnet armature, wherein the valve slide is supported on this surface of the guide pin, so that it can slide in the axial direction. It is also possible to provide for the guide pin to be arranged on the end of the valve slide facing the sealing seat and for the spring element to be arranged on a side of the magnet armature facing away from the sealing seat. A support of the valve slide without a spring element and with a guide pin as a sliding bearing on each of the two axial sides of the valve slide is also possible. Alternatively, the bearing support may also be implemented without a sliding bearing by means of a spring element on each of the two axial sides of the magnet armature.

In any case, the magnet armature is supported an aligned in such a way that it can be guided without contact at least in the area of the coil. The support and alignment of the magnet armature as part of the valve slide instead take place on the two axial sides of the magnet armature. It is therefore also possible to omit a guide tube for bearing and guidance of the magnet armature, so that frictional losses and magnetic losses can be reduced and ultimately a long lifetime of the valve is achieved. In addition to exerting a spring force, the spring element fulfills another function of providing frictionless bearing support. These functions can be achieved with a single element, so that the valve according to the invention has a particularly simple and robust design with a small number of components.

The spring element preferably has a stationary connection to the valve slide and the housing or the housing parts of the valve, wherein the spring element in the relaxed state is also preferably essentially planar and extends in a plane perpendicular to the axis of displacement of the valve slide. The spring element may be designed as a mold-lowering punched part, for example, from a sheet-metal type of material. However, the spring element is preferably deflected by 0.3 mm, for example, along the axis of displacement in the currentless state of the valve. The deflection of the essentially planar spring element may take place in particular based on the mechanical load acting on the magnet armature in the direction of the sealing seat, this load being generated by a prestressing spring, for example. On energization of the coil and a corresponding displacement of the valve slide against the mechanical load, the spring element is then deflected in the opposite direction, based on the planar state of the spring element, preferably by approximately the same amount, in particular because of the stationary connection to the valve slide. Greater durability is achieved due to the deflection of the spring element about its zero position, i.e., the essentially planar state, than if the spring element were deflected in only one direction.

The spring element may be a ring-shaped element with curved or essentially S-shaped spring legs, so that the valve slide is centered by means of the spring element. Such a spring element also allows axial mobility, i.e., deflection of the valve slide perpendicular to the plane of the spring element. However, it is also conceivable for the valve slide not to be secured in a stationary manner on the spring element, so that there is only a radial alignment of the valve slide by the spring element but the valve slide remains displaceable relative to the spring element in the axial direction.

The folded bellows-type sealing element is advantageously closed at one end. It may be hat-shaped or cap-shaped, for example. The sealing element is preferably arranged on the axial end of the valve slide, which faces the sealing seat in such a way that the closed end of the sealing element closes the sealing seat with a fluid-tight seal in the closed position of the valve slide. The sealing element is preferably designed as an integral component. In other words, the closed end and the folded bellows form one component and are not designed to be separate. The sealing element is preferably made of an elastic rubber material. The one-piece sealing element with the folded bellows is simpler and less expensive to manufacture than a traditional sealing element manufactured from a plurality of individual parts, in particular folded bellows made of PTFE, a separate sealing cap and an O-ring. Folded bellows made of PTFE are complex and expensive to manufacture in particular because they are manufactured by a machining method, for example. The term "folded bellows" is understood in very general terms to refer to any tubular or similarly shaped element that can be deformed in its axial direction by providing at least one fold. Folded bellows may have just one fold, for example, or may also have a plurality of folds and thus may be in the shape of an accordion.

In an advantageous embodiment, the valve slide comprises a ram, which is connected to the magnet armature on the side of the magnet armature facing the sealing seat and forms the axial end of the valve slide facing the sealing seat. The sealing element is preferably attached to the ram, so that it moves with the valve slide in displacement of the latter. For example, the sealing element together with its folded bellows may be inverted over the ram or even attached securely to the ram. The sealing element may also be vulcanized onto the ram. The ram may have a protrusion, for example, a circumferential bead, on its free axial end, over which the elastic sealing element can be inverted and thereby secured. The sealing element may have a recess accordingly, for example, a peripheral notch on its inside, which cooperates with the protrusion on the ram.

The valve preferably comprises a stop, which cooperates with the guide pin, so that it limits axial movement of the valve slide. The stop may comprise a damping element made of a rubber material, so that the movement of the valve slide is limited to a damping action when the end face of the guide pin strikes the stop. This also results in noise reduction in particular. The stop may be designed as a rubber disk, for example, which is simple and inexpensive to manufacture.

A plastic sheathing, which surrounds at least one drive part of the valve, may advantageously be provided. The plastic sheathing may protect the valve from splashed water and/or soiling, for example, according to the protection class IP54 and also serves as thermal touch protection at the same time. The plastic sheathing may be manufactured by a low-pressure injection-molding method, wherein adhesive bonding to the valve housing and sealing of same are implemented at the same time. This is less expensive and complicated than a powder coating or a recoating of the coil by the plastic injection-molding process. Sheathing by a casting compound would be more complex and more expensive and might possibly require additional sealing elements and adhesive bonding.

The valve may be provided and used in particular in a device for providing an extracorporeal circulation for treating a patient, in particular for dialysis, wherein the device comprises at least one fluid channel and at least one such valve in the fluid channel to control a fluid flow through the fluid channel. The device may be, for example, a dialysis machine for hemodialysis.

DESCRIPTION OF THE DRAWINGS

A preferred exemplary embodiment of the invention is described below as an example on the basis of the accompanying drawings, in which:

FIG. 2 shows a spring element comprised of the valve from FIG. 1, and

FIG. 3 shows schematically a dialysis machine having the valve from FIG. 1.

DETAILED DESCRIPTION OF THE INVENTION

Figure 1:
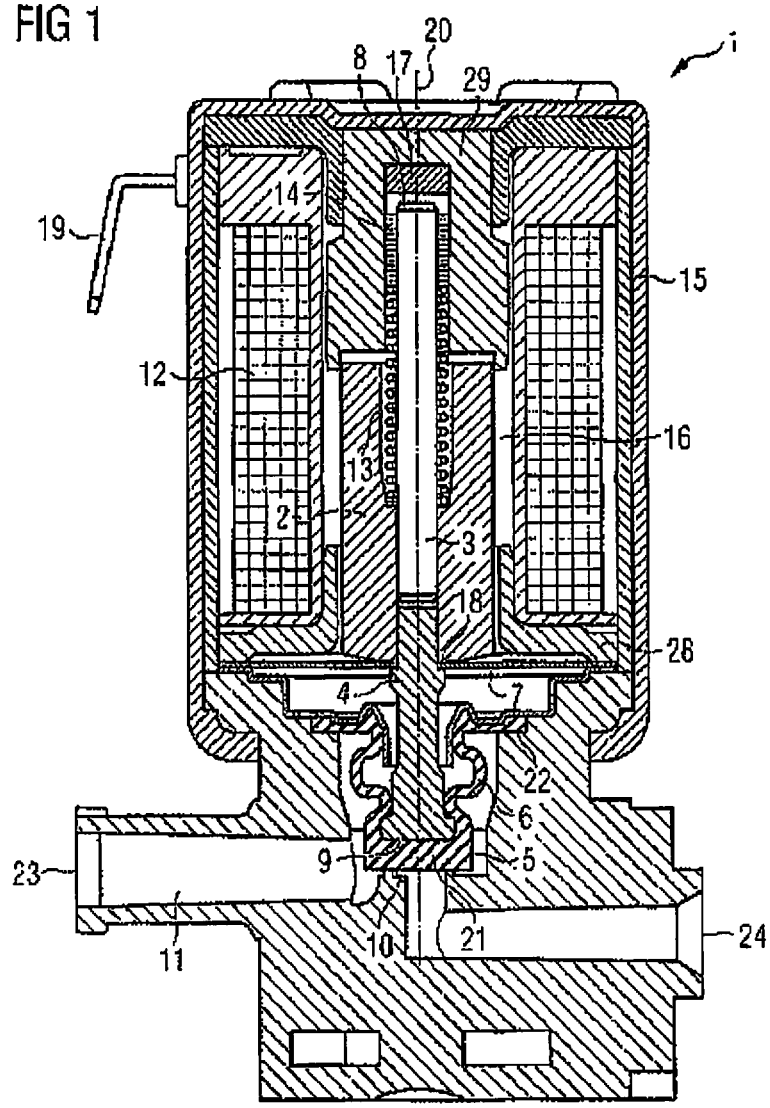
FIG. 1 shows a valve according to the invention in a sectional diagram.

FIG. 1 shows an electromagnetically operated valve 1, which may be used as a dialysis valve in particular. The valve 1 is provided for controlling a fluid flow in a fluid channel and/or a dialysis machine. To do so, a sealing seat 10 in a fluid channel 11 may be opened and closed between the inlet and outlet ends 23, 24 of the valve 1. The valve 1 has a valve slide that is axially displaceable along an axis of displacement 20 and comprises a magnet armature 2, a guide pin 3 and a ram 4, which are connected to one another by a press fit. The magnet armature 2 forms a part of the so-called magnetic circuit of the valve 1 and is moved in the axial direction by means of the magnetic force generated by a coil 12. In this exemplary embodiment, the magnet armature 2 is moved out of the closed position against the force of a spring 13 and in the direction of a stationary pole part 29. The magnetic force also acts axially against the force of a spring element 7 that is provided for support and alignment of the valve slide, as will be explained in greater detail below. If the coil 12 is switched off as shown here, the valve slide is forced in the direction of the sealing seat 10, closing it with its axial end 9 that faces the sealing seat 10.

A sealing element 5 is arranged between the valve slide and the sealing seat 10. More precisely, the sealing element 5 sits on the free axial end of the ram 4, which at the same time forms the axial end 9 of the valve slide facing the sealing seat 10. The free end of the ram 4 has a protrusion, for example, a circumferential bead or rib, so that the sealing element 5 is held securely on the ram 4. The sealing element 5 has a closed end 21, which is forced by the valve slide against the sealing seat 10 to close same. Fixedly clamped bellows 6, which can be deformed axially and thus allow an axial movement of the valve slide, are connected to the closed end 21 of the sealing element 5. The sealing element 5 is clamped securely and with a seal in the valve housing, with its end 22 facing away from the sealing seat 10. In this way, the valve slide is separated from the fluid channel 11 by a fluid-tight means and does not come in contact with fluid, which is important in medical applications in particular.

On the side of the magnet armature 2 facing the sealing seat 10, the valve slide is supported by means of a spring element 7. The valve slide is therefore aligned radially and at the same time is movable axially. The spring element 7 is shown in a top view in FIG. 2. It is designed to be planar in the relaxed state and has a central opening 27, into which the valve slide is inserted. The spring element 7 is deflected in the direction of the sealing seat 10 by 0.3 mm, for example, along the axis of displacement in the currentless state of the valve 1, i.e., when the coil 12 is shut down. There is a radial centering of the valve slide by means of curved or essentially S-shaped arms 26. The ram 4 is accommodated in the central opening 27 of the spring element 7. In this exemplary embodiment, the spring element 7 with its inner edge is clamped between the magnet armature 2 and a flange 18 of the ram 4, so that it is stationary with respect to the valve slide. The outer edge of the spring element 7 is in turn connected in a stationary position to housing parts of the valve 1. There is therefore a deflection of the spring element 7 perpendicular to a plane when the valve slide moves in the axial direction along the axis of displacement 20. The spring element 7 is then deflected by approximately the same amount in the opposite direction, based on the planar state of the spring element 7, by which it is deflected in the currentless state, i.e., by approximately 0.3 mm, for example. During the movement of the valve slide, it remains aligned and centered in the radial direction due to the spring element 7.

On its axial end 8 opposite the sealing seat 10, the valve slide has a guide pin 3, which protrudes away from the magnet armature 2 in the axial direction. The guide pin 3 is pressed at one end into the magnet armature 2. The other end is supported in a sliding bearing 14 so that it is axially movable. The guide pin 3 may be made of steel or brass, for example. The sliding bearing 14 may be made of plastic or steel, for example, wherein a PTFE coating may also be used. The spring 13, which is supported on the sliding bearing 14, sits in a borehole in the magnet armature 2 on its opposite end. In this exemplary embodiment, the force of the spring 13 pushes the valve slide into the closed position.

Due to the special guidance of the magnet armature 2, namely due to the radial alignment by means of the spring element 7, on the one hand, and due to the guidance by means of the guide pin 3 in the sliding bearing 14, on the other hand, it is possible for the magnet armature 2 itself to be supported in an essentially noncontact manner. An additional guide tube in the interior of the coil 12 may be omitted. Instead of that there is an air gap 16 between the magnet armature 2 and the coil 12. Due to the noncontact support of the magnet armature, there is no friction that would increase the wear or the necessary magnetic forces. Magnetic losses are reduced due to the omission of a guide tube, which must be designed to be nonmagnetic. Furthermore, the air gap between the magnet armature 2 and a flow guide disk 28 may be designed to be smaller due to the omission of the guide tube, so that the losses in the magnetic circuit are lower.

The axial movement of the guide pin 3 is limited by a stop 17 when the free axial end 8 strikes against the stop 17. The stop 17 is designed here as a sound-absorbing rubber disk and can be manufactured in a particularly simple and inexpensive manner, for example, as a molded part or as a punched part. The rubber disk in particular is advantageous in comparison with O-rings which may be used as an alternative damping element because O-rings have the disadvantage that they have a limited shape and a limited damping effect.

A plastic sheathing 15, which surrounds at least the drive part of the valve 1, i.e., that part of the valve which accommodates the magnetic circuit with the coil 12 is provided. The plastic sheathing 15 protects the valve 1 from splashing water and soiling according to type of protection IP54. In addition, the plastic sheathing 15 offers a thermal touch protection. This thermal insulation is provided because the valve can heat up during operation. Electric power terminals 19 pass through the plastic sheathing 15. The plastic sheathing can be produced by low-pressure injection molding, for example, which is simpler and less expensive than powder coating of the valve housing or protection by a casting compound.

FIG. 3 shows schematically a dialysis machine 50 with the valve 1. More extensive details about the dialysis machine 50 are not shown for the sake of simplicity. The dialysis machine 50 has an input line 52 for supplying blood from a patient to be cleaned as well as an output line 53 for returning the cleaned blood back to the patient. The blood is pumped through the circuit by means of a blood pump 54. Furthermore, an input line 55 is provided for supplying fresh dialysate and an output line 56 is provided for removing the spent dialysate. The dialysate is pumped through the lines 55, 56 by means of a dialysate pump 57. The actual dialysis is performed by means of a dialysis membrane 51, with the patient's blood being passed by one side of the membrane 51 and the dialysate being passed by the other side. At least one valve 1 is provided in the dialysate circulation to control the flow of the dialysate. For example, up to 30 or 50 such valves may be used in a dialysis machine. FIG. 3 shows a valve 1 in each of the lines 55, 56 schematically and as an example.

The invention claimed is:

1. An electromagnetically operated valve, comprising:
an axially displaceable valve slide, which is equipped to close a sealing seat in a fluid channel of the valve with a first axial end in a closed position;
a sealing element with folded bellows situated between the sealing seat and the first axial end of the valve slide and separating the valve slide from the fluid channel with a fluid-tight seal;
an axially movable magnet armature as part of the valve slide; and
an electrically energizable coil,
wherein the magnet armature can be moved into the closed position or out of the closed position by electrical energization of the coil against a mechanical load acting on the magnet armature to move the valve slide,
characterized in that the valve slide is aligned in the radial direction and is movably supported in the axial direction by at least one spring element planar in the relaxed state on at least one of its axial ends.

2. The valve according to claim 1, wherein the valve slide has a guide pin protruding in the axial direction away from the magnet armature on the second axial end opposite the first axial end, said guide pin having a surface with a reduced diameter in comparison with the outside diameter of the magnet armature, wherein the valve slide is supported so it slides in the axial direction on this surface of the guide pin, and the valve slide is aligned in the radial direction on the side of the magnet armature facing the first axial end of the valve slide so that it is movably supported by the at least one spring element.

3. The valve according to claim 1, wherein the valve slide has a guide pin which protrudes in the axial direction away from the magnet armature and the side of the magnet armature facing the first axial end of the valve slide, such that the guide pin has a surface with a reduced diameter in comparison with the outside diameter of the magnet armature, wherein the valve slide is supported, so that it slides in the axial direction on this surface of the guide pin, and the valve slide is aligned in the radial direction and is supported so that it is movable in the axial direction on the second axial end, which is opposite the first axial end, by the at least one spring element.

4. The valve according to claim 1, wherein the at least one spring element is connected in a stationary connection to the valve slide and a housing of the valve.

5. The valve according to claim 1, wherein the sealing element is closed at one end and is arranged on the first axial end of the valve slide, such that the closed end of the sealing element seals the sealing seat in a fluid-tight connection in the closed position of the valve slide.

6. The valve according to claim 1, wherein the at least one spring element is an annular element with curved or essentially S-shaped spring legs, so that the valve slide is centered by the spring element.

7. The valve according to claim 1, additionally comprising a plastic sheathing, which surrounds at least one drive part of the valve.

8. The valve according to claim 1, wherein the at least one spring element planar in the relaxed state extends in a plane perpendicular to the axis of displacement of the valve slide.

9. The valve according to claim 8, wherein the at least one spring element is deflected in the direction of the sealing seat in the currentless state of the valve and can be deflected in the opposite direction when the coil is electrically energized.

10. The valve according to claim 1, wherein the valve slide comprises a ram, which is connected to the magnet armature on the side of the magnet armature facing the first axial end of the valve slide, and forms the first axial end of the valve slide.

11. The valve according to claim 10, wherein the sealing element is attached to the first axial end of the valve slide on the ram, such that it also moves with a displacement of the valve slide.

12. The valve according to claim 1, further comprising a stop, which cooperates with the guide pin, so that it limits an axial movement of the valve slide.

13. The valve according to claim 12, wherein the stop comprises a damping element made of a rubber material.

14. A device for providing an extracorporeal circulation for treatment of a patient comprising at least one fluid channel and at least one valve according to claim 1 in the at least one fluid channel to control a fluid flow through the at least one fluid channel.

15. The device according to claim 14, wherein the treatment is dialysis.

16. In a method comprising extracorporeal blood circulation for treatment of a patient using a device comprising at least one fluid channel, the improvement comprising the valve according to claim 1 in the at least one fluid channel to control fluid flow through the at least one fluid channel.

17. The method according to claim 16, wherein the treatment is dialysis.

* * * * *